United States Patent [19]

Maan

[11] Patent Number: 4,639,131
[45] Date of Patent: Jan. 27, 1987

[54] DEVICE FOR MEASURING THE STATIC LIVES OF OPTICAL FIBERS

[75] Inventor: Nicolaus Maan, Eindhoven, Netherlands

[73] Assignee: U.S. Philips Corporation, New York, N.Y.

[21] Appl. No.: 774,422

[22] Filed: Sep. 10, 1985

[30] Foreign Application Priority Data

Sep. 18, 1984 [NL] Netherlands ............... 8402857

[51] Int. Cl.$^4$ ............................................. G01N 21/84
[52] U.S. Cl. ........................................ 356/73.1; 73/830
[58] Field of Search ............... 356/32, 33, 34, 73.1; 73/760, 828, 830; 65/29, 160

[56] References Cited

U.S. PATENT DOCUMENTS 4,501,492  2/1985  Douklias ..................... 356/73.1

OTHER PUBLICATIONS

Jackson et al., "A Technique for Estimating the Breaking Strain of Long Lengths of Optical Fibres", J. Phys. E.: Sci. Instrum., vol. 11, No. 2, Feb. 1978.

Primary Examiner—Eugene R. LaRoche
Assistant Examiner—Robert J. Pascal
Attorney, Agent, or Firm—Marc D. Schechter

[57] ABSTRACT

An arrangement for measuring the static lives of glass optical fibers. The arrangement comprises a number of holders. In each holder a rod with a fiber wound on it can be arranged. The holder surrounds each rod on three sides. Upon rupture of a fiber the broken ends strike the enclosure and eject the rod from its holder. Means are provided for recording the instants of insertion and ejection of each rod in and from a holder.

6 Claims, 2 Drawing Figures

DEVICE FOR MEASURING THE STATIC LIVES OF OPTICAL FIBERS

BACKGROUND OF THE INVENTION

The invention relates to an arrangement for measuring the static life of optical fibers. The arrangement comprises a cylindrical rod on which a fiber can be wound under stress.

Optical communication channels, in which long optical glass fibers are used, require reliable and predictable strength and life characteristics. Many examinations have already been carried out regarding the strength and life of fibers with respect to environmental influences. These examinations have shown that due to a number of parameters, the strength and life can be materially reduced. This means that during the manufacturing process the fiber should constantly be tested in order that the production process may be readjusted with reference to the test results.

To obtain information about static fatigue of fibers, the rod test is used. In the rod test a number of pieces of fiber of equal length are wound under a given stress on rods of different diameters, and the time which elapses until the fibers ruptures is measured. To be able to ascertain a relationship between stress and life for a given kind of fiber, a large number of test results is required, in which the times elapsing between the beginning and end (rupture) of the test can differ greatly.

SUMMARY OF THE INVENTION

It is an object of the invention to provide an arrangement in which a large number of static fiber tests can be carried out simultaneously and in which the instants at which the test begins and ends are determined automatically.

The arrangement according to the invention comprises a number of holders in each of which a rod with a fiber wound on it can be arranged. Each holder is enclosed on three sides by an enclosure. The enclosure is so arranged that upon rupture of a fiber the broken ends of the fiber strike the enclosure to produce a reaction on the fiber which ejects the respective rod from its holder. Means are provided for recording the instant of insertion of a rod in a holder and the instant of ejection of the rod from the holder.

A surprising aspect of this arrangement is that the fibers break more or less explosively. As a result, the broken ends of a ruptured fiber will strike the enclosure with some force and the resulting reaction on the fiber will eject the rod on which the fiber is wound from its holder.

The means for detecting the instants of insertion and ejection of a rod in and from a holder may be of various kinds. According to a preferred embodiment, they are a light source and a photosensitive cell which are located at opposite ends of an inserted rod.

Another possibility is to manufacture the rod from an electrically conductive material and to arrange the holding points of the holders as part of an electric circuit which is closed upon insertion of a rod in a holder and is interrupted upon ejection of the rod from the holder.

Thus, the instants of insertion and ejection can be very readily detected for each holder, and can be stored through suitable means in a memory included in the arrangement. This memory may be fixedly in the arrangement, or it may be a removable tape or disk memory.

With the arrangement according to the invention, a very large number of test lengths of fiber wound on rods of different diameters can be tested simultaneously, so that an idea about the properties of the fiber is obtained in a comparatively short time.

DESCRIPTION OF THE PREFERRED EMBODIMENTS

Figure 1:
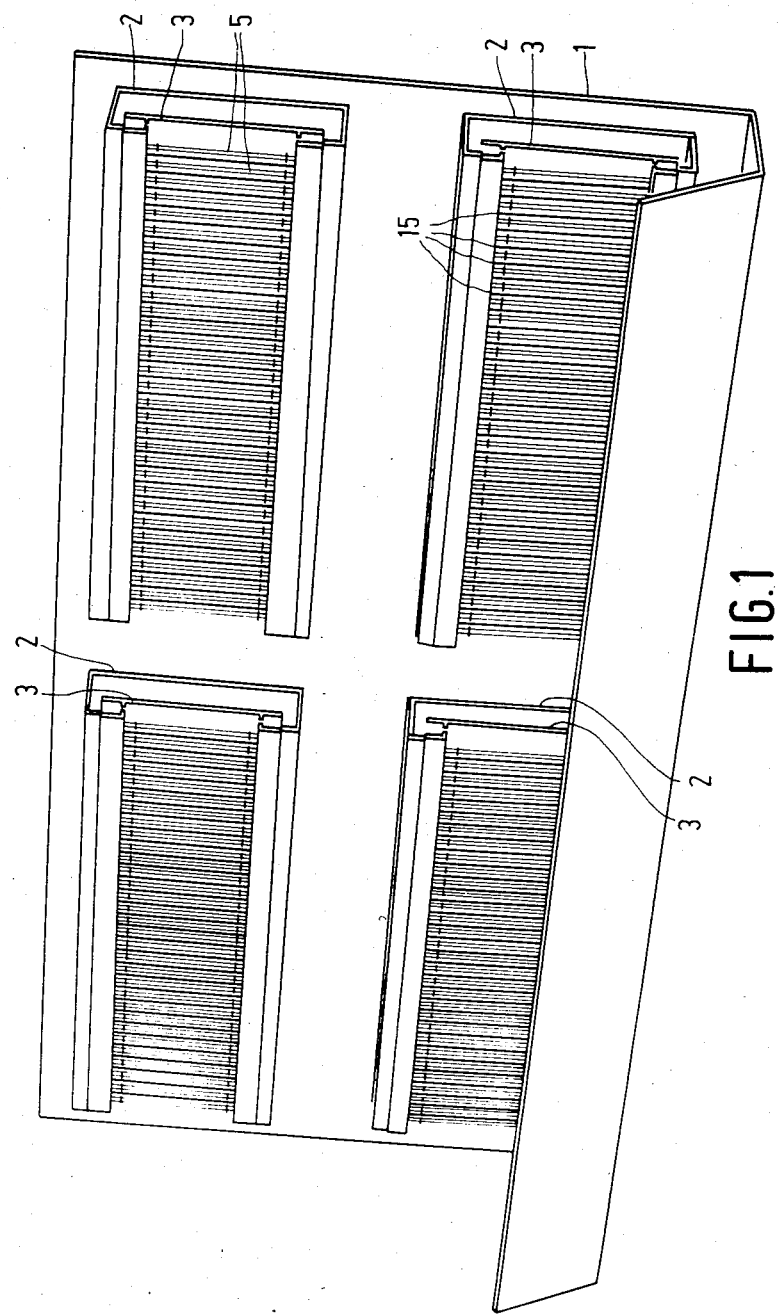
FIG. 1 is a perspective view of an embodiment of an arrangement according to the invention for measuring the static life of optical fibers. The arrangement comprise four frames each having a number of holders in which rods can be arranged.
Figure 2:
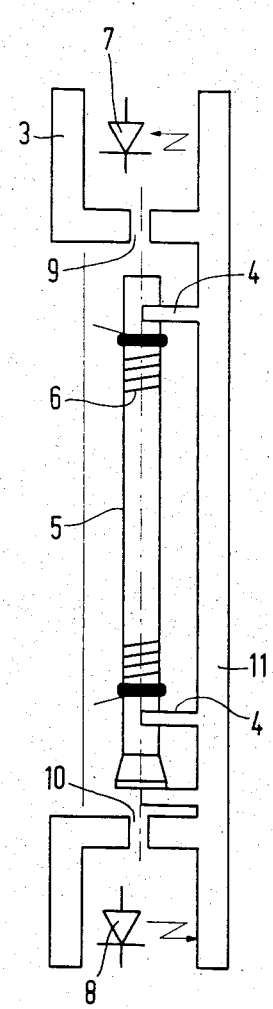
FIG. 2 is a schematic sectional side elevation, drawn to an enlarged scale, of one of the frames.

The arrangement shown in FIGS. 1 and 2 comprises a back plate 1 which carries four devices 2, each supporting a frame 3. Each of these frames 3 is provided with thirty-two holders 4. Each holder comprises a pair of spaced holder elements, in each of which a rod 5 is loosely arranged. A length of optical fiber 6 is wound under stress on each of the rods 5.

Each frame 3 is provided at the area of each holder 4 with a light source 8 and a photosensitive cell 7. Source 8 and cell 7 are arranged opposite light passages 10 and 9, respectively. The rod 5 is arranged between these two passages.

The light sources 8 are all connected through electrical conductors (not shown) to a current source.

The photosensitive cells 7 are all connected through conductors to a recording device, which is not shown in the drawing but which may be of any conventional type. A partition wall 15 is arranged between every two adjacent holders so that each rod is enclosed on three sides.

The operation of the arrangement is as follows. Upon rupture of a fiber 6, the broken ends of the fiber strike the back wall 11 of the frame 3 or an adjacent partition wall 15. The rod 5 upon which that fiber is wound is ejected by the resulting reaction force from its holder 4 so that a light path is opened between the passages 9 and 10.

The instant of ejection of this rod 5 is then recorded by the recording device so that in due course the lives of all the test lengths of fiber are known. If rods of different diameters have been arranged in the different frames 3, within a comparatively short time a relationship can be determined between the stress in the fiber and the instant of rupture.

With the arrangement according to the invention, a large amount of data is obtained within a comparatively short time, and this data is recorded automatically. In order to prevent the rods from falling out of their holders due to shocks or vibrations, the back plate 1 and hence also the frames 3 are arranged so as to be inclined backwards slightly.

What is claimed is:

1. An apparatus for measuring the static lives of glass optical fibers, said apparatus comprising:
   a number of cylindrical rods, each rod being wound with an optical fiber under stress;
   a number of holders, each holder holding one rod;
   a number of three-sided enclosures, each enclosure surrounding each holder on three sides such that on rupture of a fiber the broken fiber ends strike the enclosure to eject the rod on which the fiber was wound from its holder; and means for recording the times rods are inserted in holders and the times rods are ejected from holders.

2. An apparatus as claimed in claim 1, characterized in that the recording means comprises:

a number of light sources, one light source arranged at a first end of each rod; and a number of photosensitive cells, one photosensitive cell arranged at a second end of each rod opposite each light source.

3. An apparatus as claimed in claim 2, characterized in that the apparatus further includes memory means for storing the times rods are inserted and ejected.

4. An apparatus as claimed in claim 1, characterized in that:

each rod is electrically conductive; and each holder and its rod form an electric circuit which is opened when the rod is ejected from the circuit.

5. An apparatus as claimed in claim 4, characterized in that the apparatus further includes memory means for storing the times rods are inserted and ejected.

6. An apparatus as claimed in claim 1, characterized in that the apparatus further includes memory means for storing the times rods are inserted and ejected.

* * * * *